United States Patent
Dettinger et al.

(10) Patent No.: US 6,667,286 B1
(45) Date of Patent: Dec. 23, 2003

(54) ADHESIVE SANITARY AGENT

(75) Inventors: Johannes Dettinger, Horb (DE); Edgar Jaeschke, Filderstadt (DE); Detlef Seidel, Esslingen (DE)

(73) Assignee: Buck-Chemie GmbH (DE)

(*) Notice: Subject to any disclaimer, the term of this patent is extended or adjusted under 35 U.S.C. 154(b) by 0 days.

(21) Appl. No.: 09/701,985

(22) PCT Filed: Jun. 4, 1999

(86) PCT No.: PCT/EP99/03866

§ 371 (c)(1),
(2), (4) Date: Dec. 6, 2000

(87) PCT Pub. No.: WO99/66017

PCT Pub. Date: Dec. 23, 1999

(30) Foreign Application Priority Data

Jun. 12, 1998 (DE) .......................... 198 26 293

(51) Int. Cl.$^7$ .............................. C11D 17/00
(52) U.S. Cl. ................ 510/191; 510/193; 510/403; 510/470; 510/473; 510/475; 134/42
(58) Field of Search ................ 510/193, 191, 510/470, 473, 475, 403; 134/42

(56) References Cited

U.S. PATENT DOCUMENTS

| | | | |
|---|---|---|---|
| 3,578,499 A | 5/1971 | Crotty et al. | 134/4 |
| 3,681,141 A | 8/1972 | Muoio | 134/41 |
| 5,047,167 A | * 9/1991 | Steyn et al. | 252/160 |
| 5,460,742 A | 10/1995 | Cavanagh et al. | 252/144 |
| 5,466,395 A | 11/1995 | Tosaka et al. | 252/551 |

FOREIGN PATENT DOCUMENTS

| | | |
|---|---|---|
| CA | 1 151 501 | 8/1983 |
| DE | 2 288 186 A | 10/1995 |
| DE | 195 25 604 A1 | 1/1997 |
| DE | 197 15 872 A1 | 10/1998 |
| EP | 0 589 761 A1 | 3/1994 |
| GB | 2288186 | * 10/1995 |
| WO | WO 95/18209 | 7/1995 |
| WO | WO 95/21239 | 8/1995 |
| WO | WO 97/04061 | 2/1997 |
| WO | WO 97/40133 | 10/1997 |
| WO | WO 98/46712 | 10/1998 |

OTHER PUBLICATIONS

JP60141797—Derwent Summary.

* cited by examiner

*Primary Examiner*—Necholus Ogden
(74) *Attorney, Agent, or Firm*—Blank Rome LLP

(57) ABSTRACT

The invention relates to a sanitary agent for cleaning and/or disinfecting and/or releasing an odorant, said agent comprising an adhesion promoter, water anionic and/or nonionic and/or amphoteric surface active agents and, optionally, further common constituents such as odorants, thickeners, colorants and preservatives. The adhesion promoter is selected from the group of very long or long-chained organic molecules which are hydrophilic at least in part. The hydrophilic part of the adhesion promoter interacts at least in part with the water molecules in the presence of water and becomes "sticky" so that the agent can be applied directly on the sanitary object in the presence of small amounts of water and can adhere thereto. The viscosity of the agent is of at least 15,000 mPas and the product can only be washed away completely after numerous rinsings. The invention also relates to a method for applying a sanitary agent, wherein the agent is directly applied on the surface of the sanitary object to be cleaned and adheres to said surface.

20 Claims, No Drawings

ADHESIVE SANITARY AGENT

This is a U.S. National Phase Application of PCT/EP99/03866, filed Jun. 4, 1999, which in turn is based on German Application No. 198 26 923.0 filed Jun. 12, 1998, the subject matter of both being incorporated herein by reference.

The invention concerns a sanitary agent for cleaning and/or disinfecting and/or releasing a deodorant for sanitary objects such as toilet bowls. It is known to hang sanitary agents in the water tank by means of appropriate hanging devices, whereby from there the release of the sanitary agent takes place evenly with each flushing action in the toilet bowl. Sanitary agents are also known for use in toilet hang-in baskets, which are attached through a holder to the toilet bowl edge, whereby the sanitary agent is released with each flushing action.

A disadvantage with these known devices is its replacement by hand with a new sanitary agent, for example, in the form of a toilet cleaning block, in the existing uptake system when the sanitary agent has been used up. Among the users there exists a psychological block about putting a new one in the device after using up the sanitary agent, especially in the case of the toilet hang-in basket, whose refilling requires putting one's hand in the toilet bowl. The take-up devices that go there are only partly and with difficulty accessible on the unhygienic places, and replacing the agent is associated with a certain expenditure of time. Moreover, the conventional toilet hang-in basket causes problems due to the hanger-shaped holder if one wishes to clean the toilet bowl edge by hand where the holder is attached.

Another disadvantage with the toilet hang-in basket is that, during cleaning with the toilet bowl brush, it can, for example, be easily displaced and then must be put on the desired place again by using one's hands, which is unhygienic. Also disadvantageous about the hang-in basket is that in some cases it can be considered a toy by children and can be removed from the edge of the bowl. Usually a single toilet hang-in basket is used on a sanitary object so thatch the effect of the sanitary agent is locally limited and the amount is limited by the maximum filling capacity of the hang-in basket and/or the size of the sanitary agent to be used.

Such sanitary agents that are used in appropriate hanging devices are known in the form of solid blocks and recently also in gel form. Such gel-shaped sanitary agents can be filled according to need and not only when the entire sanitary agent is completely used up. Of course, with these gel-shaped sanitary agents, which, for instance, are described in DE 197 15 872, it is also necessary to refill them in the hanging device, which is considered by consumers to be unhygienic.

Moreover, sanitary agents are known and freely available on the market that are usually applied to the toilet bowl in liquid form from bottles from time to time-to then be flushed away immediately during the next flushing action. Accordingly a new application of the sanitary agent is necessary for each cleaning and/or disinfection action, which on the one hand is connected with a corresponding expenditure of time and on the other hand leads to a quick consumption of the sanitary agent with corresponding frequent cleaning, especially with daily cleaning. The cleanliness to be obtained with the liquid cleaners is also not lasting, and not everyone immediately takes a sanitary agent in the hand when the toilet gets dirty, whether in the private or public arena. In DE 195 25 604, which concerns a liquid, acidic cleaning agent for the removal of calcium, it is suggested that a thickener be mixed in with the acidic cleaning agent to increase the viscosity and thus improve the removal of calcium—especially on vertical surfaces. Of course, this publication teaches us that the viscosity of a liquid cleaning agent cannot be increased at one's desire because when it is, the removal of calcium build-ups and the necessary distribution of the cleaner cannot be attained anymore.

Difficulties with a hygienic and time-saving cleaning agent also occur with urinals. They are usually cleaned with a liquid cleaning agent, which is nonetheless immediately flushed away so that the cleaning flushing and the odor of freshness and cleanliness do not last. The urinals must therefore be cleaned continually.

The "hang-in basket solution," which is felt to be unhygienic by consumers due to the necessary replacement of the agent and which nonetheless guarantees a longer lasting cleaning and release of deodorant, cannot be realized in urinals in most cases due to the shape of the urinal and the lack of a suitable hanging edge. To obtain a longer lasting cleaning of the urinal and release of a deodorant one is aided by the use of "toilet stones," which are thrown in the toilet bowl or discharge water. They are, however, partly flushed away by the flush stream and also lead to undesired sprays. In some cases garbage such as cigarette butts are also thrown into the urinals so that cleaning personnel must sort out the "toilet stones" from the garbage in the urinal bowl when the "toilet stones" are not flushed away together with the trash.

Starting with this prior art, the problem that the invention seeks to solve is to make a sanitary agent available that obtains a long-lasting cleaning and/or deodorant-releasing and/or disinfecting effect and that can be applied in a simple and hygienic manner.

A problem of this sort is solved by a sanitary agent with the properties of claim 1.

SUMMARY OF THE INVENTION

Amazingly, it was determined that it is possible to produce a sanitary agent that can be put directly on the surface of the sanitary object to be cleaned and that adheres there so that the known holders for the sanitary agents that are felt to be unhygienic can be abandoned; this was achieved by using an adhesion promoter, namely long or long-chained organic molecules with at least one hydrophilic residual together with water in the sanitary agent.

Through the interaction between the hydrophylic part of the adhesion-promoting molecule and water especially the surface of the agent becomes "sticky," which makes an application directly onto the surface of the sanitary object possible. The application can take place with any suitable device such as a spray, tube, cartridge, spray nozzle, etc. The consumer only activates the applicator; contact with a possibly dirtied toilet hang-in basket is avoided.

The agent according to the invention can thus be applied and renewed in a hygienic way without touching the possibly dirtied facilities associated with the toilet bowl.

A considerable advantage of the agent according to the invention consists in the fact that it can be apportioned according to the desires of the consumer. If the consumer wants an intensive release of deodorant or if the toilet is used frequently, the consumer can use correspondingly larger amounts.

The agent according to the invention can also be applied in a simple way on different places of the sanitary object at the same time, for instance, to obtain a consistent cleaning effect both on the right and left side of a toilet bowl.

The agent according to the invention can also be applied in various compositions on various places on a sanitary object. This makes possible, for instance, that two incompatible components, for example, a halogen-releasing agent and an oxidation-sensitive fragrance, can be used by separating them locally for a common cleaning and/or deodorizing of the toilet.

The agent can be "sticky" either through a certain water content already in the formulation to be applied or the adhesion can be obtained by a light dampening of the surface—for example, by activating the flush water—and then applying the agent.

The adhesion obtained is so good on the sanitary object even with an application on a vertical surface that the agent does not become detached with the additional action of the streams of rinse water.

As a result of the adhesion promoter's hydrophilic part, the adhesion promoter detaches together with the residual sanitary agent little by little so that no undesired "sticky places" remain on the sanitary object, as is the case, for instance, with a simple "taping" of the sanitary agent with the double-sided adhesive tape.

The adhesion promoter nonetheless causes not only the adhesive bond with water, but usually also forms network-like structures that give the agent the necessary dimensional stability, even when under the strong action of rinse water.

It is assumed that through the network-like structure, which forms the adhesion-promoting molecules, that a decrease in the detachment speed of the agents is created so that the agent is washed away from the sanitary object only after a large number of rinsing actions. In this way the agent displays a high durability, namely without the necessity of the known release devices in the form of toilet hang-in baskets or holders for the water tank and without the reluctant, time-consuming replacement of the agent. Due to the extended durability and the high number of rinsing actions that go along with it, a new application is only needed in large time periods, which again saves time.

The molecules of the adhesion promoter are long or long-chained, for the most part linear, molecules that are at least in part hydrophilic and thus include at least a hydrophilic residual or a hydrophilic group so that the interaction with the water molecules takes place to form "sticky places." Preferably there should be unbranched molecules with these adhesion promoters to make possible the formation of the desired network.

The adhesion promoter can either be totally hydrophilic or partly hydrophilic, partly hydrophobic.

As a pure adhesion hydrophilic promoter one can use, for example, polyethelene glycol, polywax, cellulose, especially sodium carboxymethyl cellulose, hydroxyethyl cellulose, hydroxypropyl cellulose, or polysaccharides such as xanthan gum, agar agar, gellan gum, acacia gum, carob bean flour, or guar gum or starch. Polysaccharides can already form networks with the necessary solidity and a sufficient stickiness in concentrations under 10 percentage by weight, under 5 percentage by weight, and in part between 1 and 2 percentage by weight.

The adhesion-promoting molecules can be synthetic or natural polymers, for instance, polyacrylates, polysaccharides, polyvinyl alcohols, or polyvinyl pyrrolidones.

It is similarly possible to use alginates, diurethanes, gelatines, pectines, oleyl amines, alkyl dimethyl amine oxides, or alkyl ether sulfates.

Organic molecules with a hydrophilic and hydrophobic end can also be used as adhesion promoters. As hydrophilic residuals, for instance, polyalkoxy groups, preferably polyethoxy, polypropoxy, or polybutyoxy or mixed polyalkoxy groups such as, for example, poly(ethoxypropoxy) groups can be used. Especially preferred for use as a hydrophilic end, for example, is a polyethoxy residual consisting of between 15 and 55 ethoxy groups, preferably between 25 and 45 and especially preferred 35+/−5 ethoxy groups.

Anionic groups, for instance sulfonates, carbonates, or sulfates, can be used as hydrophilic ends.

Also stearates, especially sodium or potassium stearate, are suitable as adhesion promoters.

If the adhesion-promoting molecules also have a hydrophobic end, especially straight-chained alkyl residuals are suitable for the hydrophobic residual, whereby especially even-numbered alkyl residuals are especially preferred because of the better biological degradability. To obtain the desired network formation of the adhesion-promoting molecules, the molecules should be unbranched.

If alkyl residuals are chosen as hydrophobic residuals, the alkyl residuals with at least twelve carbon atoms are preferred. Especially good results were obtained with an alkyl chain length between 16 and 30 carbon atoms, especially 20 and 22 carbon atoms.

Preferred adhesion promoters are polyalkoxyalkanes, preferably a mixture of $C_{20}$ to $C_{22}$ alkyl ethoxylate with 35 EO, but also sodium dodecylbenzene sulfonate. With a reduction of the number of alkoxy groups the adhesion promoter becomes more lipophilic, whereby, for example, the solubility of perfume and thus the intensity of the fragrance can be raised.

Molecules that generally act like thickeners in aqueous systems, for example, hydrophilic substances, can also be used as adhesion promoters.

The concentration of the adhesion promoter to be used depends on its hydrophilicity and its power to form a network. When using polysaccharides, for example, concentrations between 1 and 2 percentage weight of the adhesion promoter can be sufficient, whereas when using polyalkoxyalkanes the concentrations can be between 10 and 40 percentage by weight, preferably between 15 and 35 percentage by weight, and especially preferred between 20 and 25 percentage by weight.

In order to produce the desired number of sticky places with the adhesion-promoting molecules through the absorption of water, the formulation should contain at least 3 percentage by weight water, preferably between 3 and 60 percentage by weight. The share of water depends, among other things, on the adhesion promoter used.

In addition to the components according to the invention, the sanitary agents can include other usual components such as perfume oil, a disinfection agent, preservatives such as isothiazolone derivatives or foam stabilizers such as coconut fatty acid amidopropyyl betaine or coconut fatty acid amidopropyl dimethyl amine oxide or coconut fatty acid mono/diethanolamide, but also colorants and/or substances that dissolve calcium or urine deposits, especially acids.

It is also possible to mix in olefin sulphates and/or acid methyl tauride as foaming agents with a self-cleaning action with the agent according to the invention.

If desired, one can also add salts such as sodium sulfate to raise the dissolving speed. The salt share can be up to 10 percentage by weight, preferably up to 5 percentage by weight.

The sanitary agents according to the invention can be rinsed away only after a large number of rinsing actions. The number of rinsing actions, of course, depends on the composition of each particular sanitary agent, the applied amount, and the geometry of the applied sanitary agent.

Fragrance and aromatic substances can be added to the agent to improve the room's air, whereby the exclusive consideration here is to apply such fragrances and aromatic substances to a toilet bowl. The sanitary agent can be used for other sanitary objects such as urinals, public toilets, as well as for hand-washing basins and the like.

Preferably the agent according to the invention is produced in the form of salve-like, pasty, and/or creme gels that stick to the hard surfaces through adhesion amazingly well. The gels are essentially dimensionally stable so that they do not "run" or "drip." The adhesion and form of the gels remain intact despite the considerable power (friction, deformation, . . . ) caused by the water rinse. Preferably these pasty gels include approximately 10–25 percentage by weight fragrance, 1–5 percentage by weight anionic tensides, 20–30 percentage by weight nonionic tensides, part as adhesion promoters, 0.5–1 percentage by weight thickeners, and 0.1–0.5 percentage by weight preservatives, as well as 3–60 percentage by weight water.

Preferably α-olefin sulfonate or methyl tauride as anionic tensides and alkyl($C_{20}$, $C_{22}$)ethoxylate with 35 EO, preferably 15–25 percentage by weight as an adhesion promoter and nonionic tenside, especially 0.1–3 percentage amine oxide, especially preferred approximately 1–2 percentage by weight coconut fatty acid amidopropyl diemthyl amine oxide (35%) will be used as a foam stabilizer and thickener. Xanthan gum is used as a further adhesion promoter and isothlazolone derivatives are used as preservatives.

The gels are applied to the toilet bowl preferably through tubes, comparable to toothpaste tubes, sprays, or cartridges and adhere there during a multitude of successive rinse actions.

The viscosity of these pasty gels, determined by a Haake viscosimeter, is at least 15,000 mPas, usually at least 25,000 mPas, preferably at least 35,000 mPas, and especially preferred at least 60,000 mPas.

It is likewise possible to develop the sanitary agent as a deodorant-releasing and/or cleaning and/or disinfecting rigid gel, which preferably includes anionic tensides, adhesion promoters, amphoteric tensides, glycols and derivatives, water, perfume, and preservatives. The rigid gels are basically firm and can be stuck to the moist or dry surface by means of an application device, which preferably makes possible cutting the rigid agent at the desired length. The firm gels can be produced and applied in the form of disks, blocks, or other separable pieces. The viscosity of the rigid gels, measured with a Haake viscosimeter, should be at least 50,000 mPas, especially preferred at least 150,000 mPas.

The sanitary agents can also be thixotropic fluids or fluids that harden in some manner after being applied, whereby the viscosity of the agent should be at least 15,000 mPas after being applied.

If a further increase in durability is to be obtained, one can also add thickeners such as silicates to the sanitary agent.

In principle it is also possible to conceive of the agent basically as a pure fragrance agent that is "stuck" to a surface. The agent could be used, for instance, in cars, garbage cans, etc.

The agent according to the invention is usually produced through the interaction of the components with water.

In the following the sanitary agent according to the invention is illustrated in greater detail by using a working example and comparative tests.

1. EXAMPLE FORMULA FOR A SANITARY AGENT AS A PASTY GEL

| Components | Content (%) | Brand Name/ Supplier | Function |
|---|---|---|---|
| α-olefin sulfonate | 1–5 | Hostapur OSB (Clariant) | anionic |
| alkyl($C_{22}$)-ethoxylate (35 EO) | 20–25 | Imbentin V 100 (Dr. W. Kolb AG) | adhesion promoter |
| coco amido propyl dimethyl amine oxide (35%) | 1–3 | Rewominox B 204 (Witco Surfactants) | foam stabilizer thickener |
| xanthum gum | 0.5–1 | Rhodopol T (Rhone Poulenc) | adhesion promoter |
| isothiazolone derivates | 0–1 | Parmetol K40 (Schülke & Mayr) | preservatives |
| water | 3–60 | | |
| perfume | 15–25 | Citrix II 98-1103 (Quest International) | fragrance |

2. COMPARATIVE TESTS

A pasty gel in accordance with the above formula 1 was compared to two conventional sanitary cleaners with respect to their behavior when being applied to the porcelain surface, the adhesion, and the durability depending on the number of rinses.

From a tube with a nozzle opening of 6×26 mm, 10 ml of three sanitary agents were applied to a toilet bowl directly under the rinse stream.

| | Behavior when applying it to the surface | Behavior when actuating the rinse action |
|---|---|---|
| gel-shaped pasty sanitary agent according to working example I | sticks as a rectangular caterpillar | used up in 100 to 200 rinses depending on formulation |
| bottle 00 toilet cleaner with fumed silica (firm Yankee Polish); formula according to DE 195 604 Al | because fluid, it can't be dosed through a nozzle; is distributed as a fluid over the toilet bowl | after 2 rinses the cleaner does not adhere anymore to the porcelain surface |
| toilet fresh gel (firm Henkel) formula according to DE 197 15 872 A | runs immediately in unattractive streaks in the direction of the toilet outlet | after 3 rinses there is only about 20% left on the porcelain surface; after 5 rinses the gel is completely washed away |

What is claimed is:

1. Sanitary agent for direct application to a sanitary object to be cleaned comprising:

an adhesion promoter selected from the group consisting of long and long-chained organic molecules, which are at least partly hydrophilic, and the hydrophilic part of the adhesion promoter interacts at least in part with the water molecules in the presence of water and becomes "sticky" which enables said agent to adhere to said sanitary object even after a large number of rinse actions;

water;

anionic and/or nonionic and/or amphoteric tensides;

and optional components selected from the group consisting of fragrances, thickeners, colorants, preservatives, and combinations thereof;

wherein the viscosity of the agent is at least 15,000 mPas.

2. Sanitary agent according to claim 1, wherein the adhesion promoter is hydrophilic and is chosen from a group consisting of polyethylene glycol, cellulose, polysaccharides, and starches, whereby the cellulose is selected from the group consisting of sodium carboxymethyl cellulose, hydroxyethyl cellulose, and hydroxypropyl cellulose and the polysaccharides is selected from the group consisting of xanthum gum, agar, gelatin gum, acacia gum, carob bean flour, guar gum, and combinations thereof.

3. Sanitary agent according to claim 1, wherein the adhesion promoter is chosen from the group consisting of alginates, diurethanes, gelatins, pectines, oleyl amines, alkyl diemethyl amine oxides, alkyl ether sulfates, alkyl ethoxylate, stearates, alkali metal stearates and combinations thereof.

4. Sanitary agent according to claim 1, wherein the adhesion promoter is partly hydrophilic and the hydrophilic part of the adhesion promoter is an alkyl residual.

5. Sanitary agent according to claim 4, wherein the alkyl residual has at least twelve carbon atoms, preferably between 16 and 30 carbon atoms.

6. Sanitary agent according to claim 1, wherein the hydrophilic residual of the adhesion promoter includes a sulfonate or sulfate or a polyalkoxy group, whereby the polyalkoxy group is selected from the group consisting of polyethoxy, polypropoxy, polybutyoxy, and a mixed polyalkoxy group.

7. Sanitary agents according to claim 1, wherein the concentration of the adhesion promoter is between 10 and 40 percentage by weight.

8. Sanitary agent according to claim 1, wherein the adhesion promoter is synthetic or natural polymers selected from the group consisting of polyacrylate, polysaccharide, polyvinyl alcohol, polyvinyl pyrrolidone, starch and mixtures thereof.

9. Sanitary agent according to claim 1, in the form of a pasty or firm gel.

10. Sanitary agent according to claim 1 having a viscosity which is at least 25,000 mPas.

11. Sanitary agent according to claim 4, wherein the alkyl residual is unbranched having an even number of carbon atoms.

12. Sanitary agent according to claim 4, wherein the alkyl residual has between 16 and 30 carbon atoms.

13. Sanitary agent according to claim 12, wherein the alkyl residual has between 20 and 22 carbon atoms.

14. Sanitary agent according to claim 4, wherein the concentration of the adhesion promoter is between 10 and 40 percentage by weight.

15. Sanitary agent according to claim 6, wherein the concentration of the adhesion promoter is between 10 and 40 percentage by weight.

16. Sanitary agent according to claim 1, wherein the sanitary agent is a rigid gel and includes glycols.

17. Sanitary agent according to claim 5, wherein the alkyl residual has between 16 and 30 carbon atoms.

18. Sanitary agent according to claim 5, wherein the alkyl residual has between 20 and 22 carbon atoms.

19. Sanitary agent according to claim 1 having a viscosity that is at least 35,000 mPas.

20. Sanitary agent according to claim 1 having a viscosity that is at least 60,000 mPas.

* * * * *